United States Patent [19]

Usukura

[11] 4,231,356

[45] Nov. 4, 1980

[54] SURGICAL IMMOBILIZING BANDAGE AND THE LIKE

[75] Inventor: Koji Usukura, Kasukabe, Japan

[73] Assignee: Tokyo Eizai Lab. Co., Ltd., Tokyo, Japan

[21] Appl. No.: 954,467

[22] Filed: Oct. 25, 1978

[30] Foreign Application Priority Data

Nov. 17, 1977 [JP] Japan .................. 52-138244

[51] Int. Cl.³ ........................... A61F 13/04
[52] U.S. Cl. ........................ 128/90; 560/182
[58] Field of Search .............. 128/89, 90; 526/272; 560/1, 182

[56] References Cited

U.S. PATENT DOCUMENTS

| | | | |
|---|---|---|---|
| 3,459,736 | 8/1969 | Dalibor | 560/182 |
| 3,483,166 | 12/1969 | Kibler et al. | 560/182 |
| 4,044,761 | 8/1977 | Hall | 128/90 |

Primary Examiner—C. Fred Rosenbaum
Attorney, Agent, or Firm—Robert E. Burns; Emmanuel J. Lobato; Bruce L. Adams

[57] ABSTRACT

A surgical immobilizing bandage and the like which are quite excellent in various properties of moldability, durability, lightness in weight, water resistance, X-ray transmittance and so forth. The surgical immobilizing bandage of the invention is composed of the main constituent of an aliphatic polyester polymer or a mixture of aliphatic polyester polymers which are synthesized from aliphatic diols and saturated dicarboxylic acids. Further, the above bandage is prepared by impregnating an elastic fabric with a composition containing the above aliphatic polyester polymers, coloring agents and fillers.

7 Claims, No Drawings

SURGICAL IMMOBILIZING BANDAGE AND THE LIKE

BACKGROUND OF THE INVENTION

1. Field of the Invention

This invention relates to a surgical immobilizing bandage and the like for use in the formation of orthopedic casts. More particularly, the invention relates to a surgical immobilizing bandage and the like which are used for the purposes of immobilization, fixation and protection of affected parts in orthopedic surgery, especially, in the treatment of dislocation, sprain and fracture of bones.

2. Description of the Prior Art

In the conventional art, a gauze-like fabric is applied with or impregnated with calcined gypsum (plaster of Paris) and it is wound into a rolled web to be stored. When the gypsum-containing immobilizing bandage is used in surgical treatment, it is soaked in water, then taken out and wound again and again round an affected part which is previously swathed in a cotton or knit bandage, until the treated part becomes desirably stable and strong. Meanwhile, the immobilizing bandage becomes gradually hard due to the curing which is caused by the hydration of gypsum, thereby fixing the affected part.

It is quite important that the immobilizing bandage fits well to affected parts and it must be durable in a long time use without causing any undesirable trouble during the medical treatment and patient's daily life. The above-mentioned immobilizing bandage with gypsum is widely used since the calcined gypsum has good moldability. It is, however, defective in water resistance and is liable to be broken. In addition, the gypsum-containing bandage is hardly transmissible to X-rays, is large in weight and stains clothes and bedclothes. Therefore, various kinds of plastic immobilizing bandages have been proposed until now and many patent applications on such materials have been filed. However, any of them is still inferior to the gypsum-containing bandage in view of the moldability.

SUMMARY OF THE INVENTION

It is, therefore, the primary object of the present invention to provide an improved surgical immobilizing bandage and the like which are free from the above-described disadvantages in the conventional art.

Another object of the present invention is to provide a surgical immobilizing bandage and the like which are quite good in moldability so as to be well fit to any affected part.

A further object of the present invention is to provide a surgical immobilizing bandage and the like which have many other desirable properties such as excellent durability, water resistance and X-ray transmittance.

Still a further object of the present invention is to provide a surgical immobilizing bandage and the like which are light in weight and large in hardness.

In accordance with the present invention, the surgical immobilizing bandage and the like are mainly composed of an aliphatic polyester polymer or a mixture of aliphatic polyester polymers which are synthesized from aliphatic diols and saturated dicarboxylic acids. According to further aspect of the present invention, the surgical immobilizing bandage is prepared by impregnating an elastic fabric such as tricot knitting and rubber-threaded fabric with an immobilizing composition which is composed of a main constituent of an aliphatic polyester polymer or a mixture of aliphatic polyester polymers and coloring agents and/or fillers.

DETAILED DESCRIPTION OF THE INVENTION

These and other objects and features of the present invention will become apparent from the following detailed description.

As written above, the aliphatic polyester polymers are synthesized from aliphatic diols and saturated dicarboxylic acids. Exemplified as such aliphatic polyester polymers are polyhexamethylene adipate, polyethylene suberate, polyethylene sebacate, polytetramethylene adipate, polytetramethylene sebacate, polyhexamethylene succinate, polyhexamethylene oxalate, polyhexamethylene pimelate, polyhexamethylene suberate, polyhexamethylene sebacate, polyhexamethylene azelate, polyoctamethylene oxalate, polyoctamethylene succinate, polyoctamethylene glutarate, polyoctamethylene adipate, polyoctamethylene pimelate, polyoctamethylene suberate, polyoctamethylene azelate, polyoctamethylene sebacate, polyeicosamethylene oxalate, polyeicosamethylene malonate, polyeicosamethylene succinate, polyeicosamethylene glutarate, polyeicosamethylene adipate, polyeicosamethylene pimelate, polyeicosamethylene suberate, polyeicosamethylene azelate, polyeicosamethylene sebacate, poly-2,2-dimethyl trimethylene malonate, poly-2,2-dimethyl trimethylene succinate, polydecamethylene oxalate, polydecamethylene succinate, polydecamethylene glutarate, polydecamethylene adipate, polydecamethylene pimelate, polydecamethylene azelate, polydecamethylene suberate, and polydecamethylene sebacate. Further, it is desirable that the melting points of the above polymers are not lower than 50° C. and the second order transition points (glass transition points) of them are lower than −20° C. so as to be crystallizable.

The above-mentioned aliphatic diols are represented by the general structural formula:

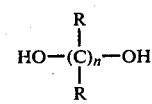

which includes saturated diols and unsaturated diols. The saturated diols having hydrogen atoms (H) as the symbol R are exemplified by 1,2-ethanediol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,15-pentadecanediol, 1,16-hexadecanediol, 1,17-heptadecanediol, 1,18-octadecanediol, 1,19-nonadecanediol, and 1,20-eicosanediol. Further, the above symbol R may be propyl group, halogen atoms (Cl, I, Br, F), cyclohexyl group or phenyl group. The unsaturated diols having hydrogen atoms (H) as the symbol R are exemplified by ethene-1,2-diol, 1-butene-1,4-diol, 2-butene-1,4-diol, and 2,2-dimethylpropane-1,3-diol.

The above-mentioned saturated dicarboxylic acids are represented by the general structural formula:

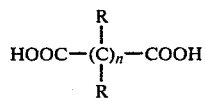

which are exemplified by oxalic acid, malonic acid, succinic acid, glutaric acid, adipic acid, pimelic acid, suberic acid, azelaic acid, and sebacic acid.

As the example of the present invention, the preparation of immobilizing compositions mainly containing the aliphatic polyester polymer of polyhexamethylene adipate will be firstly described in the following.

The polyhexamethylene adipate is synthesized from 1,6-hexanediol and adipic acid. In the synthesis, 1.05 moles of 1,6-hexanediol and 1 mole of adipic acid are mixed together and allowed to react with stirring at a temperature of 180° to 200° C. under nitrogen gas current. The reaction product is a quite viscous fluid of milk white color, and when it is cooled to an ordinary temperature, it solidifies and becomes a lumpy solid of high rigidity. It is preferable that the molecular weight of the reaction product may be at least 10,000 since the reaction product becomes frangible if the molecular weight thereof is lower than 8,000. The melting point of such a polymer is about 55° C. so that the polymer can be easily softened by heating to give adherence.

To 100 parts (by weight, the same shall apply hereinafter) of the above polyhexamethylene adipate is added 10 parts or less of titanium oxide as filler. If the ratio of titanium oxide or other inorganic filler exceeds 10 parts, the composition becomes brittle, and moldability and X-ray transmittance become worse. In order to mix the titanium oxide, the polyhexamethylene adipate is previously dissolved in an organic solvent such as trichlene or it is heated to 100 to 150° C. and titanium oxide is dispersed into the dissolved or molten polymer with sufficient stirring. The titanium oxide is preferably pulverized beforehand. In this disclosure, the mixing of titanium oxide is done by the former method to use an organic solvent. In order to color the immobilizing composition, some suitable coloring agents are added to the composition when the titanium oxide is mixed.

In the following, the supporting cloth will be described. The supporting cloths are generally classified, in view of their materials, into natural fiber, synthetic fiber and inorganic fiber. In view of the forms of them, there are paper type, unwoven fabric type and felt type ones. Further, they are classified into knitting and netting in view of the textures. In order to improve the moldability or adaptability, the knitting is quite suitable for the purpose of the present invention. As described in the foregoing, the immobilizing bandage of the present invention is wound round an affected part such as dislocation, sprain and fracture of bones to form a cast. The surfaces of a human body are curved variously, however, any large pressure cannot be exerted to the affected part. The surgical immobilizing bandage must be exactly applicable to such the affected part. For this purpose, the supporting cloth is desirably elastic and deformable. When the immobilizing bandage is used in a tape-like form, the elasticity in the longitudinal direction is important as compared with the elasticity in the lateral direction, however, the material which is elastic in both directions is quite suitable for the supporting cloth of immobilizing bandage because it can be deformed quite easily. Exemplified as the supporting cloth which is elastic in both directions, is a knitted fabric of tricot. The elasticity of tricot can be further improved by entwining spandex yarn or rubber string which is covered with cotton or rayon. Such an elastic supporting cloth is soaked into a composition which is composed of polyhexamethylene adipate dissolved in an organic solvent and titanium oxide. The supporting cloth is fully impregnated with the composition under the application of pressure by passing it through a pair of rollers. The impregnated fabric is then led into an oven while nothing must be brought into contact with the impregnated fabric. The organic solvent is then completely volatilized off from the fabric by hot blast of 40° to 100° C. After that, a corrugated film of polyethylene is put in layers on the product and it is wound into a rolled web. The rolled web is then divided at a certain width, thereby forming a finished tape-like immobilizing bandage.

The immobilizing bandage of the present invention is used in like manner as the aforementioned method to use the conventional gypsum-containing bandage. That is, the immobilizing bandage of the invention is softened in hot water of 50° to 100° C. to make it adhesive, and it is wound again and again round an affected part which has been previously covered by cotton or knit bandage. The immobilizing bandage is applied to the affected part until the uniform thickness of the bandage becomes sufficient to fix the affected part. In this application of the bandage, the corrugated polyethylene film is of course peeled off, so that the layers of bandage are bonded tightly. The molten composition is precisely adapted to the curved surface of a body together with the elastic supporting cloth and it serves as an immobilizing cast. In the case that the shape of solidified cast must be varied partially to some extent some other day, it is possible to deform the cast by partially heating it. This advantage cannot be expected from the conventional gypsum-containing immobilizing cast.

Described above is the composition mainly containing polyhexamethylene adipate. The present invention can be attained by a mixture of a plurality of aliphatic polyester polymers as the main component materials. The advantage of such a case will be described in the following.

For example, the main components are composed of 50 parts of polyhexamethylene adipate (hereinafter referred to as "Polymer I") and 50 parts of polyhexamethylene suberate (hereinafter referred to as "Polymer II"). The melting point of Polymer I is 55° C., while that of Polymer II is 61° C. Accordingly, the features and effects of the sole Polymer I and the mixture of Polymers I and II in the formation of immobilizing casts are different as follows. That is, the solidification of the mixture of Polymers I and II occurs earlier than that of the sole Polymer I, however, the possible times of fused adhesion are not different. With regard to the formed casts, the thermal resistance of the mixture of Polymers I and II is higher than that of the other one. In view of the above fact, it is possible to prepare a most suitable and serviceable immobilizing bandage for each purpose by using two or more of aliphatic polyester polymers having different melting points as the main constituent materials of the immobilizing bandage.

Although the present invention has been described in connection with preferred examples thereof, many variations and modifications will now become apparent to those skilled in the art. It is preferred, therefore, that the present invention be limited not by the specific disclosure herein, but only by the appended claims.

What is claimed is:

1. A surgical immobilizing bandage and the like comprising an elastic fabric impregnated with a composition the main constituent of which consists of an aliphatic polyester polymer or a mixture of aliphatic polyester polymers which are synthesized from aliphatic diols and saturated dicarboxylic acids.

2. A surgical immobilizing bandage and the like according to claim 1, in which said composition further includes coloring agents.

3. A surgical immobilizing bandage and the like according to claim 1, in which said composition further includes fillers.

4. The surgical immobilizing bandage and the like as claimed in claim 1, wherein said aliphatic polyester polymers are polyhexamethylene adipate and/or polyhexamethylene suberate.

5. The surgical immobilizing bandage and the like as claimed in claim 1, wherein said elastic fabric is tricot or rubber-threaded fabric.

6. The surgical immobilizing bandage and the like as claimed in claim 1, wherein the molecular weights of said aliphatic polyester polymers are not less than 10,000, the melting points thereof are 50° C. or above, and the second order transition points thereof are lower than −20° C.

7. The surgical immobilizing bandage and the like as claimed in claim 1, wherein said aliphatic polyester polymer is at least one member selected from the group consisting of polyhexamethylene adipate, polyethylene suberate, polyethylene sebacate, polytetramethylene adipate, polytetramethylene sebacate, polyhexamethylene suberate, polyhexamethylene succinate, polyhexamethylene oxalate, polyhexamethylene pimelate, polyhexamethylene sebacate, polyhexamethylene azelate, polyoctamethylene oxalate, polyoctamethylene succinate, polyoctamethylene glutarate, polyoctamethylene adipate, polyoctamethylene pimelate, polyoctamethylene suberate, polyoctamethylene azelate, polyoctamethylene sebacate, polyeicosamethylene oxalate, polyeicosamethylene malonate, polyeicosamethylene succinate, polyeicosamethylene glutarate, polyeicosamethylene adipate, polyeicosamethylene pimelate, polyeicosamethylene suberate, polyeicosamethylene azelate, polyeicosamethylene sebacate, poly-2,2-dimethyl trimethylene malonate, poly-2,2-dimethyl trimethylene succinate, polydecamethylene oxalate, polydecamethylene succinate, polydecamethylene glutarate, polydecamethylene adipate, polydecamethylene pimelate, polydecamethylene azelate, polydecamethylene suberate, and polydecamethylene sebacate.

* * * * *